United States Patent
Jacinto

(10) Patent No.: US 9,713,520 B2
(45) Date of Patent: Jul. 25, 2017

(54) SKIRTED TISSUE REPAIR IMPLANT HAVING POSITION INDICATION FEATURE

(71) Applicant: Ethicon, Inc., Somerville, NJ (US)

(72) Inventor: Gabriel R. Jacinto, Belle Mead, NJ (US)

(73) Assignee: Ethicon, Inc., Somerville, NJ (US)

(*) Notice: Subject to any disclaimer, the term of this patent is extended or adjusted under 35 U.S.C. 154(b) by 207 days.

(21) Appl. No.: 14/753,282

(22) Filed: Jun. 29, 2015

(65) Prior Publication Data

US 2016/0374790 A1 Dec. 29, 2016

(51) Int. Cl.
*A61F 2/00* (2006.01)

(52) U.S. Cl.
CPC .... *A61F 2/0063* (2013.01); *A61F 2002/0072* (2013.01); *A61F 2210/0004* (2013.01); *A61F 2220/005* (2013.01); *A61F 2230/0004* (2013.01); *A61F 2250/0031* (2013.01); *A61F 2250/0097* (2013.01); *A61F 2310/00005* (2013.01)

(58) Field of Classification Search
CPC ............ A61F 2/0063; A61F 2002/0068; A61F 2002/0072; A61F 2230/0004; A61F 2230/0006; A61F 2230/0008; A61F 2250/0097
See application file for complete search history.

(56) References Cited

U.S. PATENT DOCUMENTS

| | | | | | |
|---|---|---|---|---|---|
| 5,634,931 | A * | 6/1997 | Kugel | ............... | A61F 2/0063 606/1 |
| 5,769,864 | A * | 6/1998 | Kugel | ............... | A61F 2/0063 602/44 |
| 5,916,225 | A * | 6/1999 | Kugel | ............... | A61F 2/0063 602/44 |
| 6,171,318 | B1 * | 1/2001 | Kugel | ............... | A61F 2/0063 602/44 |
| 6,174,320 | B1 * | 1/2001 | Kugel | ............... | A61F 2/0063 606/151 |
| 6,224,616 | B1 * | 5/2001 | Kugel | ............... | A61F 2/0063 128/898 |
| 6,290,708 | B1 * | 9/2001 | Kugel | ............... | A61F 2/0063 602/44 |
| 6,736,823 | B2 * | 5/2004 | Darois | ............... | A61F 2/0063 600/37 |
| 6,736,854 | B2 * | 5/2004 | Vadurro | ............... | A61F 2/0063 606/151 |
| 6,790,213 | B2 * | 9/2004 | Cherok | ............... | A61F 2/0063 602/44 |
| 6,800,082 | B2 * | 10/2004 | Rousseau | ............... | A61F 2/0063 606/151 |
| 7,824,420 | B2 * | 11/2010 | Eldridge | ............... | A61F 2/0063 606/151 |
| 8,182,545 | B2 * | 5/2012 | Cherok | ............... | A61F 2/0063 606/151 |

(Continued)

*Primary Examiner* — Ryan J Severson
(74) *Attorney, Agent, or Firm* — E. Richard Skula

(57) ABSTRACT

Novel tissue repair implants are disclosed. The tissue repair implants have a bottom planar base member and an upper skirt member extending about the periphery of the base member. The implants have at least one position indicating feature that alerts the surgeon if the skirt member has rolled over or displaced during fixation to tissue in order to assist in preventing fixation of the skirt in an improper position to provide an optimal surgical repair.

28 Claims, 10 Drawing Sheets

(56) References Cited

U.S. PATENT DOCUMENTS

| | | | | |
|---|---|---|---|---|
| 8,298,290 B2* | 10/2012 | Pelissier | | A61F 2/0063 606/151 |
| 8,506,582 B2* | 8/2013 | Kammerer | | A61F 2/0045 600/30 |
| 8,795,384 B2* | 8/2014 | Nelson | | A61F 2/0063 623/23.72 |
| 8,808,315 B2* | 8/2014 | Bailly | | A61F 2/0063 606/142 |
| 8,945,235 B2* | 2/2015 | Horton | | A61F 2/0063 606/151 |
| 9,005,223 B2* | 4/2015 | Cardinale | | A61B 17/0057 606/151 |
| 9,072,586 B2* | 7/2015 | Ranucci | | A61F 2/0063 |
| 9,492,261 B2* | 11/2016 | Cohen | | A61F 2/0063 |
| 2003/0078602 A1* | 4/2003 | Rousseau | | A61F 2/0063 606/151 |
| 2003/0130745 A1* | 7/2003 | Cherok | | A61F 2/0063 623/23.72 |
| 2003/0212461 A1* | 11/2003 | Vadurro | | A61F 2/0063 623/23.64 |
| 2004/0019360 A1* | 1/2004 | Farnsworth | | A61F 2/0063 606/151 |
| 2004/0215219 A1* | 10/2004 | Eldridge | | A61F 2/0063 606/151 |
| 2005/0288691 A1* | 12/2005 | Leiboff | | A61F 2/0063 606/151 |
| 2006/0064175 A1* | 3/2006 | Pelissier | | A61F 2/0063 623/23.72 |
| 2006/0253203 A1* | 11/2006 | Alvarado | | A61F 2/0063 623/23.74 |
| 2007/0123915 A1* | 5/2007 | Kammerer | | A61F 2/0045 606/151 |
| 2007/0299538 A1* | 12/2007 | Roeber | | A61F 2/0063 623/23.72 |
| 2008/0109017 A1* | 5/2008 | Herweck | | A61L 31/145 606/151 |
| 2008/0167729 A1* | 7/2008 | Nelson | | A61F 2/0063 623/23.72 |
| 2011/0224704 A1* | 9/2011 | Bailly | | A61F 2/0063 606/151 |
| 2011/0307077 A1* | 12/2011 | Pfeiffer | | A61F 2/0045 623/23.72 |
| 2013/0317527 A1* | 11/2013 | Jacinto | | A61B 17/0057 606/151 |
| 2014/0025093 A1* | 1/2014 | Horton | | A61F 2/0063 606/151 |
| 2014/0088619 A1* | 3/2014 | Cardinale | | A61B 17/0057 606/151 |
| 2015/0018851 A1* | 1/2015 | Francois | | A61F 2/0063 606/144 |
| 2015/0148824 A1* | 5/2015 | Horton | | A61F 2/0063 606/151 |
| 2015/0173882 A1* | 6/2015 | Cardinale | | A61B 17/0057 606/151 |
| 2016/0374790 A1* | 12/2016 | Jacinto | | A61F 2/0063 600/37 |

* cited by examiner

SKIRTED TISSUE REPAIR IMPLANT HAVING POSITION INDICATION FEATURE

FIELD OF THE INVENTION

The field of art to which this invention pertains is tissue repair implants, more particularly tissue repair implants having skirts.

BACKGROUND OF THE INVENTION

Hernia repair is a relatively straightforward surgical procedure, the ultimate goal of which is to restore the mechanical integrity of the abdominal wall by repairing a muscle wall defect through which an underlying section of the peritoneum and possibly part of the underlying viscera has protruded. There are various types of hernias, each with its own specific surgical repair procedure, including ventral hernias, umbilical hernias, incisional hernias, sports hernias, femoral hernias, and inguinal hernias. It is believed that most hernias are attributable to a weakness in sections of the tissues of the abdominal wall.

Even though the commonly used, conventional surgical procedures for correcting or repairing the various types of hernias are somewhat specific, there is a commonality with respect to the mechanical repair. Typically, the protrusion of the peritoneum through a muscle or abdominal wall defect results in a hernia sack containing the underlying and protruding viscera. In these procedures, the hernia sack is dissected and the viscera are pushed back into the abdominal cavity. Then, a tissue reinforcing or repair implant, such a mesh patch device, is typically implanted and secured at the site of the abdominal wall defect. Autologous tissue quickly grows into the implant, providing the patient with a secure and strong repair. In certain patient presentations, it may be desirable to suture or otherwise close the defect without an implant, although this is typically much less desirable for an optimal outcome.

One common type of hernia is a ventral hernia. This type of hernia typically occurs in the abdominal wall and may be caused by a prior incision or puncture, or by an area of tissue weakness that is stressed. There are several conventional repair procedures that can be employed by the surgeon to treat such hernias, depending upon the individual characteristics of the patient and the nature of the hernia. An often used technique is the implantation of a tissue repair implant in the intra-peritoneal location. This can be done via an open approach or a laparoscopic approach. The tissue repair implant, for example, a mesh patch, is inserted into the patient's abdominal cavity through an open anterior incision or via a trocar and positioned to cover the defect. The surgeon then fixates the mesh implant to the abdominal wall with conventional mechanical fixation or with sutures placed through the full thickness of the abdominal wall. There are a variety of such mechanical fixation devices that can be used in laparoscopic or open surgery, e.g., surgical tacking instruments.

Intraperitoneal placement of a mesh implant via an open approach may be the desired technique of repair where, for example, the layers of the abdominal wall are attenuated and a laparoscopic approach is not desired. Although such tissue repair patch implants exist and are commonly utilized for open ventral hernia repairs, there are deficiencies known to be associated with their use. The deficiencies include difficulty in handling the implants, poor visibility during handling, implantation and fixation, challenging usability and ergonomics when using a laparoscopic instrument for fixation to tissue. The commercially available tissue repair patch implants for this application typically have at least dual layers of mesh or fabric with pockets or skirts to provide for affixation to the parietal wall via the top layer or skirt. Such implants typically have a barrier layer of anti-adhesion material on the bottom viscera-facing side of the implant.

One problem associated with skirted or pocketed mesh implants for use in open ventral hernia repair procedures involves the position of the skirt or top layer when the surgeon applies surgical tacks to affix the mesh implant to the parietal wall. Since in an open procedure the surgeon typically cannot directly view the outer periphery of the skirt and the outer periphery of the bottom base layer of the implant during affixation with a conventional hernia tacking device, it is possible for a section of the skirt or top layer of the device to roll when the distal end of the tacking instrument is positioned in a pocket formed between the skirt and the top surface of the base member, causing a section of the skirt to move beyond the outer periphery of the base member. This may result in a poor repair having an inferior outcome since one or more sections of the implanted mesh may become distorted, for example wrinkled or separated from the peritoneum, possibly preventing proper tissue incorporation and also resulting in complications such as a recurrence of the hernia, surgical adhesions, etc. In addition, a section of the surface of the skirt extending beyond the periphery of the base member may come into contact with the patient's viscera, possibly causing irritation and the formation of surgical adhesions.

Accordingly, there is a need in this art for novel tissue repair implants, such as ventral hernia repair patch implants, that can be used in an open surgical procedure, and which can be affixed to tissue by a surgeon to repair a body wall defect with minimal or no mechanical distortion of the implant.

SUMMARY OF THE INVENTION

A novel tissue repair implant is disclosed. The implant has a bottom planar base member having a top surface, a bottom surface and an outer periphery. A top planar skirt member having a bottom surface, and a top surface, an inner periphery and an outer periphery, extends inwardly about the outer periphery of the planar mesh member such that a surgical instrument can be inserted between the top surface of the planar base member and the bottom surface of the skirt member. There is an access opening associated with the skirt member. The implant also has an indicating marker associated with the bottom base member and aligned with the inner periphery of the skirt member, such that the indicating marker is not visible when the skirt member is in a first neutral position. In the first neutral position, no part of the skirt member extends beyond the outer periphery of the base member. At least a section of the indicating marker is exposed and visible when a section of the skirt member is displaced radially outward beyond the outer peripheries of the skirt member and bottom base member.

Another aspect of the present invention is a novel tissue repair implant. The tissue repair implant has a bottom planar base member having a top surface, a bottom surface and an outer periphery. The base member has a first longitudinal axis and a second latitudinal axis, and a first intersection point at the intersection of the first longitudinal axis and first latitudinal axis. The implant has a first position indicator associated with the bottom mesh member and centered on the first intersection point. A top planar skirt member having a bottom surface, and a top surface, an inner periphery and an outer periphery extends inwardly about the outer periphery of the planar base member such that a surgical instrument can be inserted between the top surface of the planar base member and the bottom surface of the skirt member. The skirt member has a second longitudinal axis and a second latitudinal axis and a second intersection point at the intersection of the second longitudinal axis and the second latitudinal axis. There is an access opening associated with the skirt member. A first connecting member connects the inner periphery of the skirt member in alignment with the first longitudinal axis and the second longitudinal axis. A second connecting member connects the inner periphery of the skirt member in alignment with the first latitudinal axis and the second latitudinal axis. The first and second connecting members intersect at the second intersection point. There is a second position indicator associated with the second intersection point for determining the position of the second intersection point with respect to the first intersection point on the base member. A misalignment of the first and second position indicators is associated with and indicates a rollover of a section of the skirt member.

Yet another aspect of the present invention is a tissue repair implant. The implant has a bottom planar base member having a top surface, a bottom surface and an outer periphery. There is a first position indicator associated with the bottom base member. A top planar skirt member having a bottom surface, and a top surface, an inner periphery and an outer periphery, extends inwardly about the outer periphery of the planar base member such that a surgical instrument can be inserted between the top surface of the planar base member and the bottom surface of the skirt member. An access opening is associated with the skirt member. A second position indicator is associated with the skirt member for determining the position of the second position indicator relative to the first position indicator, wherein a movement of the second position indicator relative to the first position indicator is an indication of a rollover of a section of the skirt member.

Still yet another aspect of the present invention is a method of using the above described implants of the present invention to repair a tissue defect.

These and other aspects and advantages of the present invention will become more apparent from the following description and accompanying drawings.

DETAILED DESCRIPTION OF THE INVENTION

Figure 1:
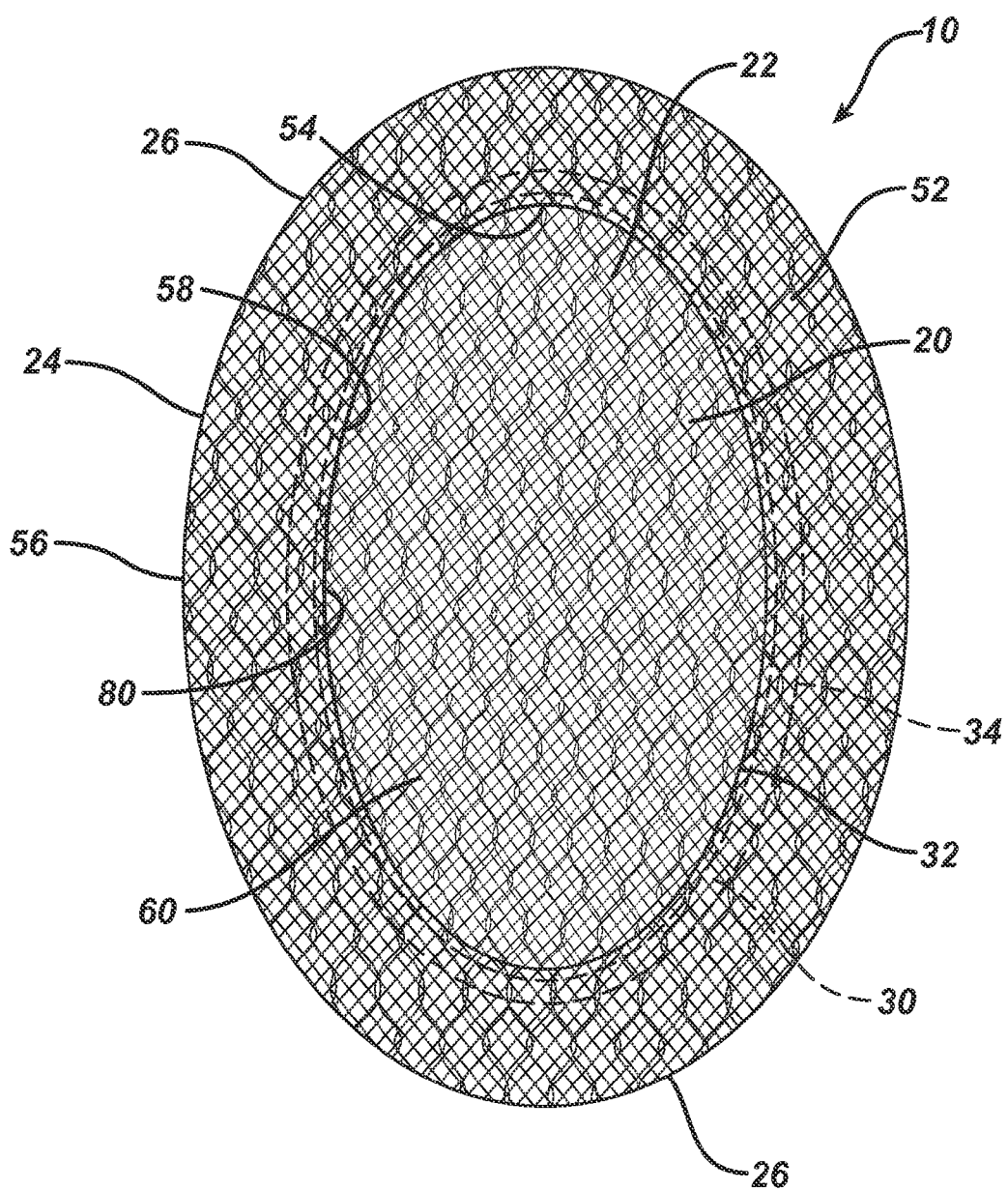
FIG. 1 is a plan view of an embodiment of a tissue repair implant of the present invention in a neutral position; the implant is seen to have a top skirt, a base member, and a position indicating feature on the base member depicted in phantom lines.
Figure 2:
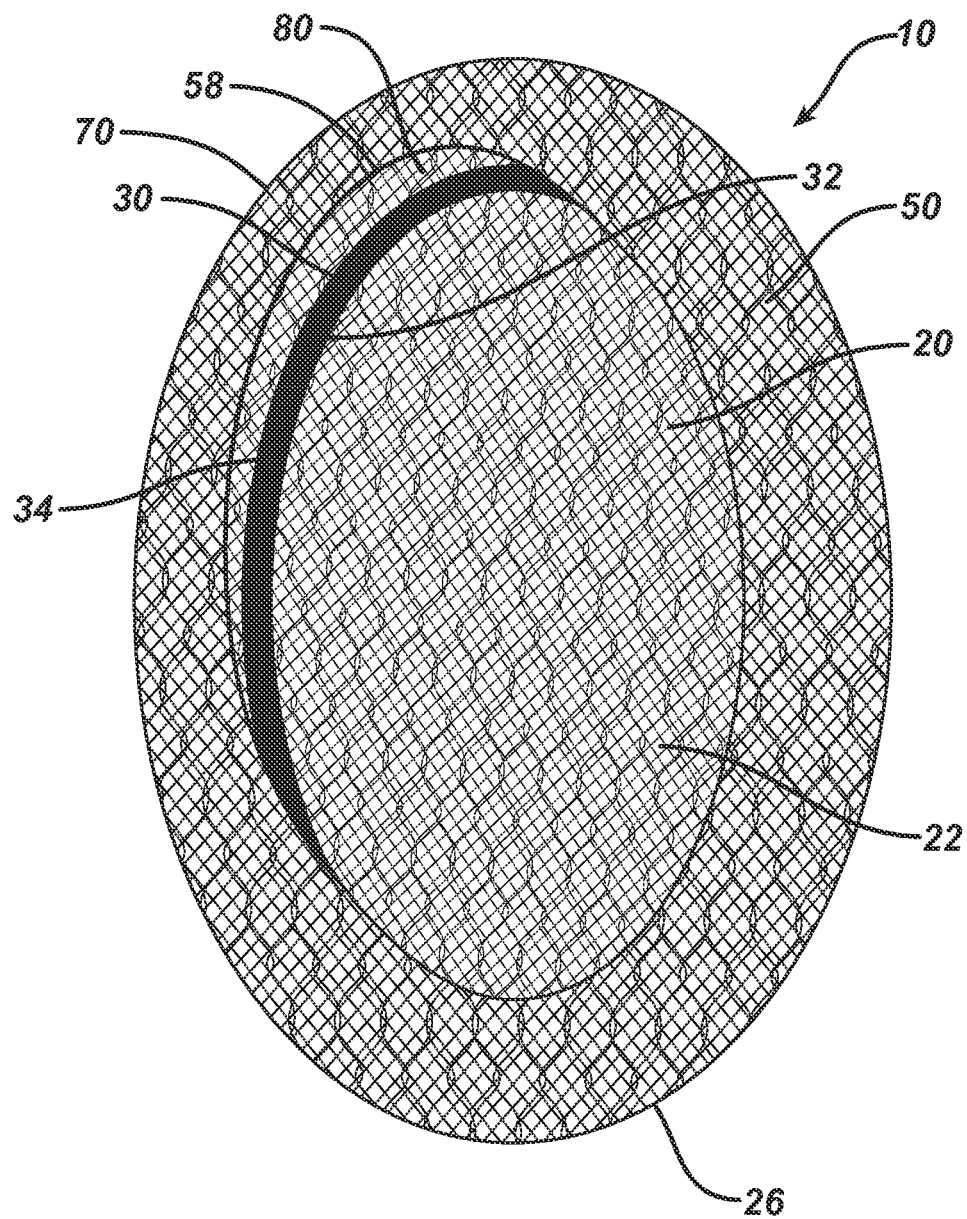
FIG. 2 is a plan view of the tissue repair implant of FIG. 1 showing a section of the skirt in a displaced position; the position indicating feature is partially visible indicating that the skirt section has been displaced and a rollover has occurred.

The novel tissue repair implants or devices of the present invention are particularly useful in open ventral or incisional hernia repair surgical procedures. The repair patch devices of the present invention have utility in other conventional tissue repair procedures including inguinal hernia repair procedures, trocar puncture wounds, trocar incisional hernias, etc.

Tissue repair implants and surgical instruments for applying tacks to fixate tissue repair implants are disclosed in the following commonly assigned, co-pending patent applications, which are incorporated by reference: U.S. Ser. Nos. 12/464,151; 12/464,165; 12/464,177; 12/464,143; 12/944,651; and, 12/815,275.

The tissue repair implants or patches of the present invention may be made from any conventional, implantable biocompatible materials. The patches and their components are preferably made from conventional, implantable biocompatible polymers that may be nonabsorbable or bioabsorbable. The term bioabsorbable is defined to have its conventional meaning and includes both biodegradable and bioresorbable. Examples of such nonabsorbable polymers include polypropylene, polyester, nylon, ultra high molecular weight polyethylene, and the like and combinations thereof. Examples of suitable bioabsorbable polymers include polylactides (PLA), polyglycolides (PGA), polydioxanones (PDO, PDS), polycaprolactones, polyhydroxy acids, polyhydroxybutyrates, polyhydroxyvaleriates and copolymers and mixtures thereof, as well as copolymers of PGA/trimethylene carbonate (TMC), copolymers of PLA/TMC, and the like.

If desired, combinations of biocompatible nonabsorbable polymers and bioabsorbable polymers may be utilized to construct the tissue repair implant patch devices of the present invention.

Although it is preferred to use surgical meshes to construct the tissue repair patches of the present invention, other conventional woven or nonwoven surgical repair fabrics or thermally formed implants may also be used. In addition, the tissue repair patches may be made from other conventional implantable materials such as PTFE (polytetrafluoroethylene), e.g., ePTFE films and laminates. The patches may consist of composites of polymeric films and meshes, and/or fabrics.

The meshes useful in the hernia repair patch devices of the present invention will be manufactured in a conventional manner using conventional manufacturing equipment and methods including knitting, weaving, non-woven techniques, and the like. The meshes will typically have a pore size sufficient to effectively provide for tissue ingrowth; for example, they may have pore sizes in the range of about 0.3 mm to about 5 mm, and other conventional size ranges. Examples of commercially available nonabsorbable and bioabsorbable polymeric meshes that may be used to construct the hernia repair patches of the present invention include ETHICON PHYSIOMESH™ and ETHICON PROCEED™ Surgical Mesh, available from Ethicon, Inc., Route 22 West, Somerville, N.J. 08876.

When constructing the novel tissue repair patches of the present invention from surgical fabrics other than meshes, the fabrics will have open pores with a pore size sufficient to effectively provide for tissue ingrowth; for example, with a typical size of about 0.3 mm to about 3 mm. By "open pores" is meant openings that extend from one side of the fabric to the opposed side, providing a pathway through the fabric. The fabric repair members may be constructed from monofilaments, multifilaments, or combinations thereof. Examples of commercially available non-mesh fabrics that can be used to manufacture the hernia repair patches of the present invention include woven fabrics, textiles and tapes for surgical applications. Other fabrics or materials include perforated condensed ePTFE films and nonwoven fabrics having pore sizes of at least one millimeter. The non-mesh fabrics may be constructed of conventional biocompatible materials.

The fabric or mesh may contain, in addition to a long-term stable polymer, a resorbable polymer (i.e., bioabsorbable or biodegradable). The resorbable and the long-term stable polymer preferably contain monofilaments and/or multifilaments. The terms resorbable polymers and bioabsorbable polymers are used interchangeably herein. The term bioabsorbable is defined to have its conventional meaning. Although not preferred, the fabric or mesh tissue repair member may be manufactured from a bioabsorbable polymer or bioabsorbable polymers without any long-term stable polymers.

The tissue repair patches of the present invention may also include polymer films. The films may be attached to the top surface, the bottom surface or both surfaces and may also cover the peripheral edges of the repair patch devices or extend beyond the periphery of the repair patch devices. The films that are used to manufacture the tissue repair patch implant devices of the present invention will have a thickness that is sufficient to effectively prevent adhesions from forming, or otherwise function as a tissue barrier or tissue separating structure or membrane. For example, the thickness may typically range from about 1 µm to about 500 µm, and preferably from about 5 µm to about 50 µm, however this will depend upon the individual characteristics of the selected polymeric films. The films suitable for use with the repair patches of the present invention include both bioabsorbable and nonabsorbable films. The films are preferably polymer-based and may be made from various conventional biocompatible polymers, including bioabsorbable and nonabsorbable polymers. Non-resorbable or very slowly resorbable substances include polyalkenes (e.g., polypropylene or polyethylene), fluorinated polyolefins (e.g., polytetrafluoroethylene or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Also useful are synthetic bioabsorbable polymer materials for example, polyhydroxy acids (e.g., polylactides, polyglycolides, polyhydroxybutyrates, polyhydroxyvalerates), polycaprolactones, polydioxanones, synthetic and natural oligo- and polyamino acids, polyphosphazenes, polyanhydrides, polyorthoesters, polyphosphates, polyphosphonates, polyalcohols, polysaccharides, and polyethers. However, naturally occurring materials such as collagen, gelantin or natural-derived materials such as bioabsorbable Omega 3 fatty acid cross-linked gel films or oxygenated regenerated cellulose (ORC) can also be used.

The films used in the tissue repair patch devices of the present invention may cover the entire outer surfaces of the hernia patch member or a part thereof. In some cases, it is beneficial to have films overlapping the borders and/or peripheries of the repair patches. The repair patches of the present invention may also have adhesion barrier layers attached to one or both sides. The adhesion barriers will typically consist of conventional biocompatible polymeric materials including but not limited to absorbable and nonabsorbable polymers. Examples of conventional nonabsorbable polymeric materials useful for adhesion barriers include expanded polytetrafluoroethylene, polytetrafluoroethylene, silicone, and the like. Examples of conventional absorbable polymeric materials useful for adhesion barriers include oxidized regenerated cellulose, poliglecaprone 25 (copolymer of glycolide and epsilon-caprolactone), and the like.

Figure 3:
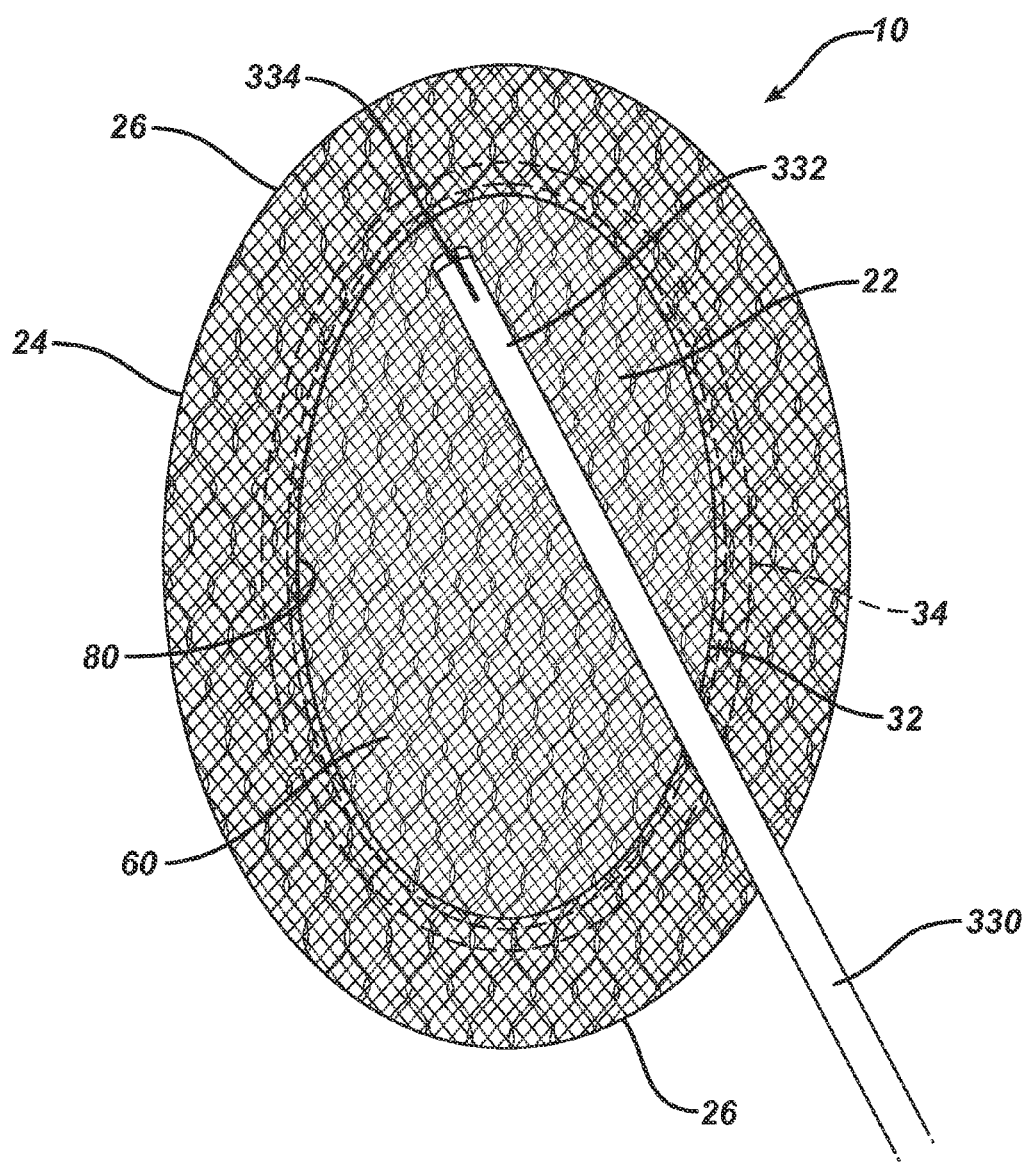
FIG. 3 is a plan view of the tissue repair implant of FIG. 1 showing the distal end of a surgical tacking instrument in position to be inserted in the pocket between the bottom base layer and the top skirt member.
Figure 4:
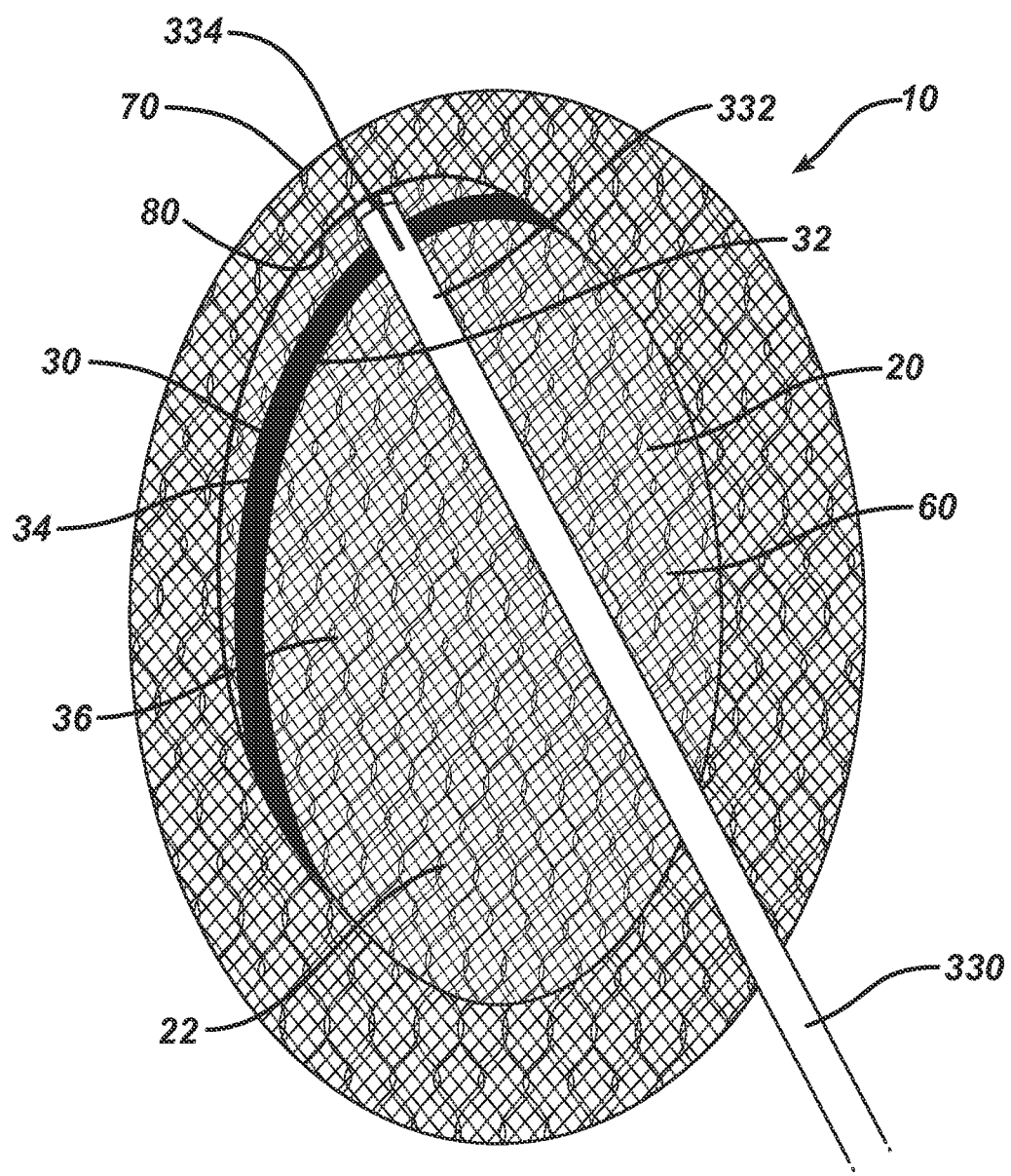
FIG. 4 illustrates the implant of FIG. 3, wherein the distal end of the tacking instrument has been moved into position to affix the top skirt to an interior surface of a body wall; the position indicator in the vicinity of the distal end of the instrument is partially visible indicating that an adjacent section of the skirt has rolled over.
Figure 5:
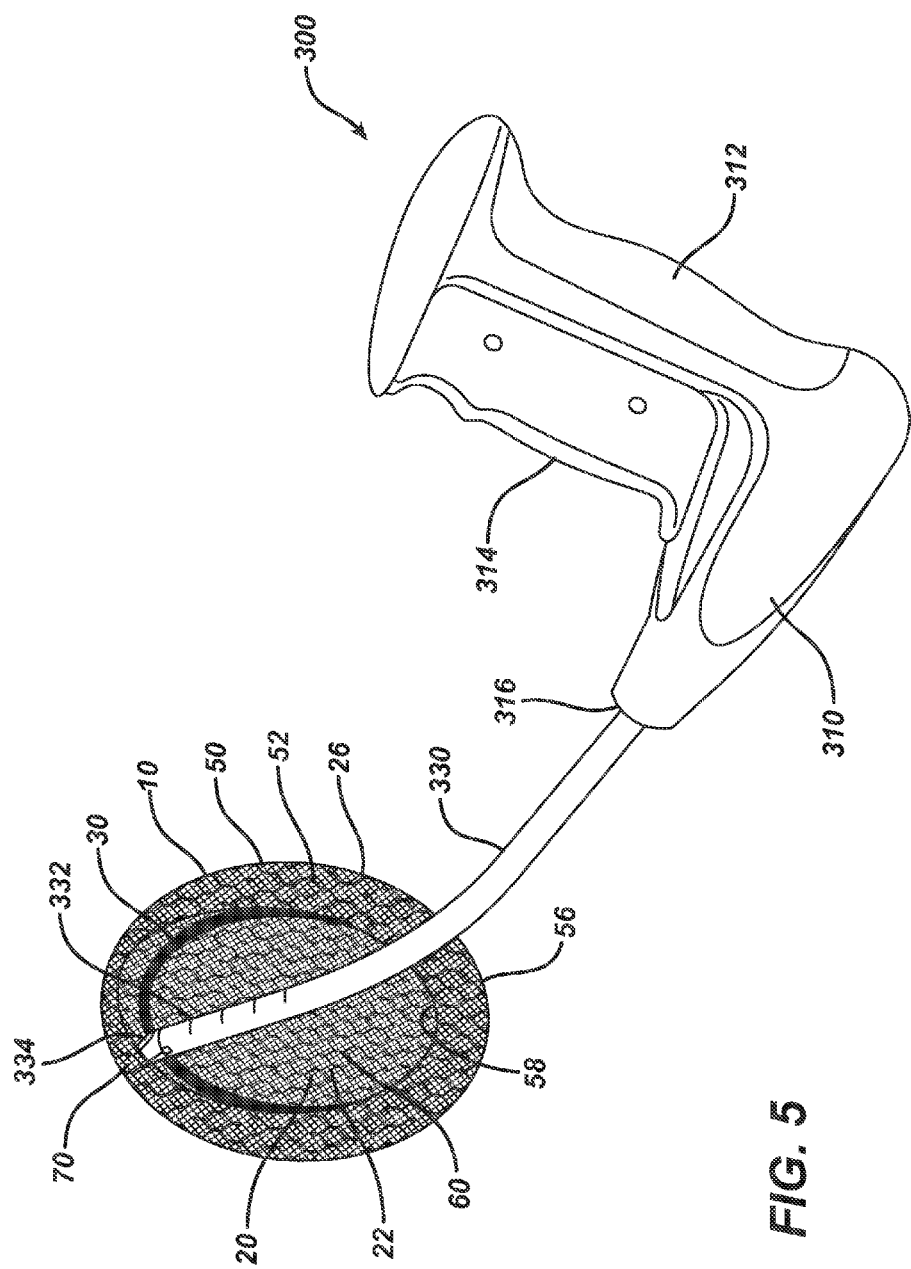
FIG. 5 is a perspective view of the implant of FIG. 4 illustrating the entire surgical tacking instrument; a section of the position indicator adjacent to the distal end of the tacking instrument is visible to the surgeon indicating a partial rollover of the top skirt.

As mentioned previously, it is particularly preferred that the tissue repair patches of the present invention have a mesh construction. Referring to FIGS. 1-5, an embodiment of a skirted mesh tissue repair implant 10 is seen. The implant 10 is seen to have planar base member 20. Base member 20 is seen to have top side 22 and bottom side 24. The base member 20 is also seen to have outer periphery 26. The base member 20 is also seen to have indicating feature 30. The indicating feature 30 is seen to be preferably located on the base member 20, but may be also woven or otherwise incorporated into base member 20. The indicating feature 30 is seen to have a ring-like construction with an inner periphery 32, an outer periphery 34, and opening 36. The indicating feature 30 is seen to have an elliptical shape, but may have other geometric configurations. The implant 10 is also seen to have skirt member 50. Skirt member 50 is seen to have top side 52, bottom side 54, outer periphery 56 and inner periphery 58. The opening 60 is defined by the inner periphery 58. The skirt member 50 may be mounted to or extend from the top side 22 of base member 20 such that the outer peripheries 26 and 56 of the base member 20 and skirt member 50 are substantially aligned and coextensive. The skirt member 50 and base member 20 form a pocket 80 between the top side 22 and the bottom side 54. The pocket 80 is accessible through opening 60. As mentioned previously, the indicating feature 50 is seen to be elliptical in shape, but may have other configurations corresponding to the inner periphery 58 of skirt member 50. When the implant 10 is in the rest or neutral position as seen in FIG. 1, the indicating feature is not visible to the surgeon. A section of the indicating feature 30, including the inner periphery 32 and the outer periphery 34 is visible to the surgeon in FIG. 2. A section 70 of the skirt member 50 is seen to have displaced or rolled over the outer periphery 26 of base member 20 creating a condition referred to as a "rollover". The indicating feature 30 is positioned on the base member 20 such that movement of the skirt member 50 resulting from a rollover event will allow the indicating feature to be visible by the surgeon. As seen in FIG. 3, the distal end of a surgical tacking instrument 300 has been placed adjacent to the interior periphery 58 of skirt member 50 and pocket 80. In FIGS. 4 and 5, the surgeon has inserted distal end 332 and distal tip 334 of the surgical instrument 300 into the pocket 80 to secure the implant 10 to tissue, but has inadvertently moved section 70 beyond periphery 26 creating a rollover. The surgical tacking instrument 300 is seen to have housing 310. Housing 310 has proximal hand grip 312, actuating trigger 314, and distal end 316. The elongated tubular member 330 extends from distal end 316. Tubular member 330 is seen to have distal end 332 and tip 334 for discharging surgical tacks.

A rollover condition will be apparent to the surgeon when at least a part of the indicating feature 30 is visible. This visual input will allow the surgeon to correct the position of the distal end 332 and distal tip 334 so that the rollover section 70 is remediated. Conversely, if the indicating feature 30 is not visible when the surgeon locates the distal tip 334 will indicate proper placement of fixating tacks about the outer periphery 58 of skirt member 50 without a rollover.

Another embodiment of a skirted mesh tissue repair implant 110 is seen in FIGS. 6-10. The implant 110 is seen to have planar base member 120 having longitudinal axis 135 and transverse, latitudinal axis 137. Base member 120 is seen to have top side 122 and bottom side 124. The base member 120 is also seen to have outer periphery 126. The base member 120 is also seen to have first indicating feature or position indicator 190. The first indicating feature 190 is seen to be preferably located on the base member 120, but may be also woven or otherwise incorporated into base member 120. The indicating feature 190 is seen to have a ring-like construction with an inner periphery 192, an outer periphery 194, and open central area 196 and a center 198. If desired, the indicating feature 190 may be solid without an open area 196. The indicating feature 190 is seen to have a circular shape, ring-like shape but may have other geometric configurations including elliptical, square, rectangular, polygonal, combinations of curved and straight sections, and the like. The implant 100 is also seen to have skirt member 150. Skirt member 150 is seen to have top side 152, bottom side 154, outer periphery 156 and inner periphery 158. The skirt member 150 is seen to have longitudinal axis 165 and transverse, latitudinal axis 167. The opening 160 is defined by the inner periphery 158. The skirt member 150 may be mounted to or extend from the top side 122 of base member 120 such that the outer peripheries 126 and 156 of the base member 120 and skirt member 150 are substantially aligned and coextensive. The skirt member 150 and base member 120 form a pocket 180 between the top side 122 and the bottom side 154. The 180 pocket is accessible through opening 160. First connecting member 200 is seen to connect two opposed sections of the inner periphery 158 of skirt member 150 along the longitudinal axes 135 and 165 of base member 120 and skirt member 150, respectively. Second connecting member 210 is seen to connect two opposed sections of the inner periphery 158 of skirt 150 along the latitudinal axes 137 and 167 of base member 120 and skirt member 150, respectively. The connecting members 200 and 210 are seen to intersect and be joined at intersection 220. Located at intersection 220 is the second indicating feature or position indicator 230. The members 200 and 210 are seen to have a strap-like configuration, but may have other configurations including cables, sutures, etc. The connecting members 200 and 210 are preferably connected at intersection 220, but if desired may optionally not be joined together, or may be configured such that one member may slide or move within an opening (e.g., a slot) in the other member. The connecting members 200 and 210 may be formed as part of skirt member 150, or formed separately and affixed to skirt member 150.

Figure 6:
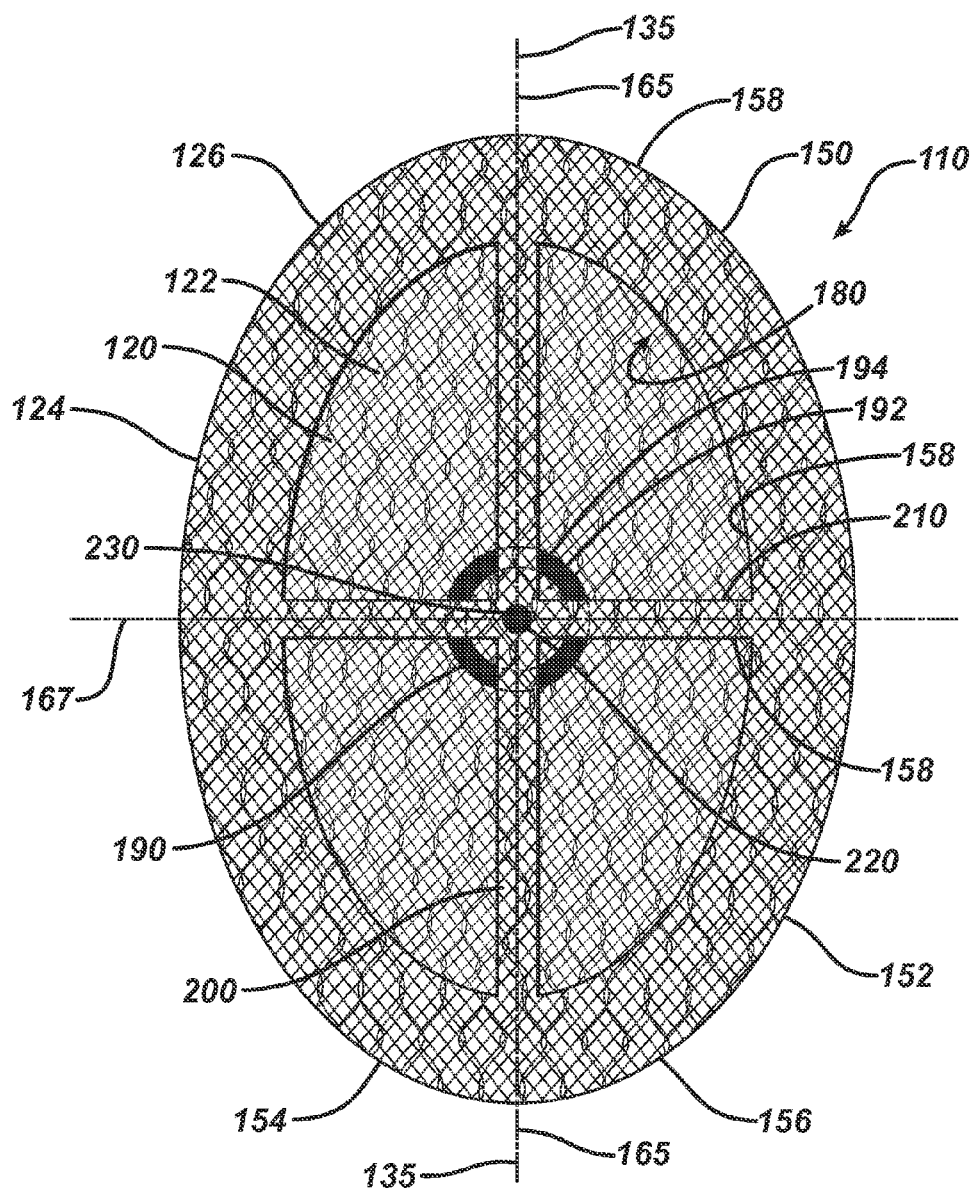
FIG. 6 is a plan view of an alternate embodiment of a tissue repair implant of the present invention in the neutral position; the implant is seen to have a base member, a top skirt and a top and bottom position indicating feature. Straps are seen to connect the inner periphery of the skirt member along the longitudinal and latitudinal axes of the implant.
Figure 7:
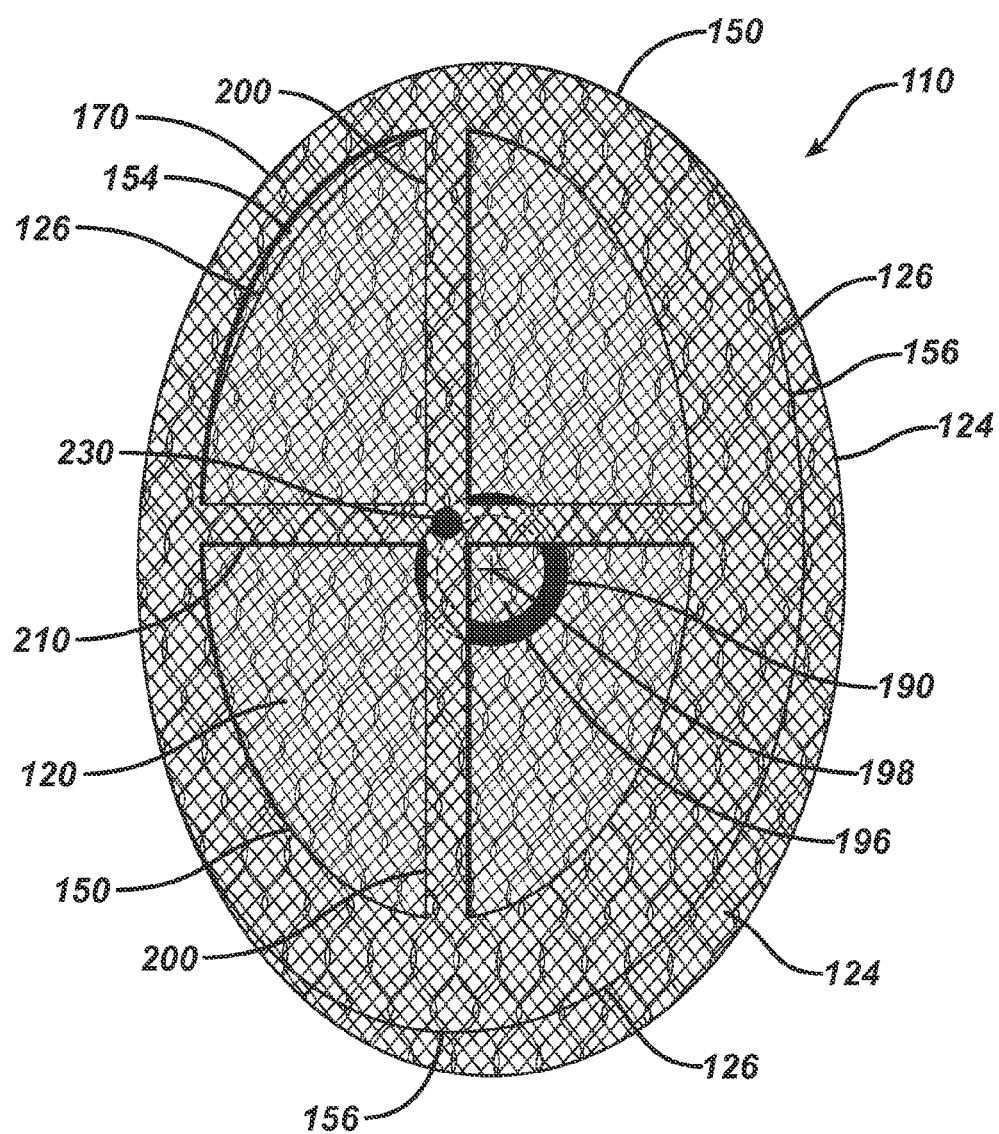
FIG. 7 is a plan view of the tissue repair implant of FIG. 6 showing the skirt in a displaced position; the top position indicating feature has been offset with respect to the bottom position indicating feature and shows that the skirt has been displaced and a rollover has occurred.
Figure 8:
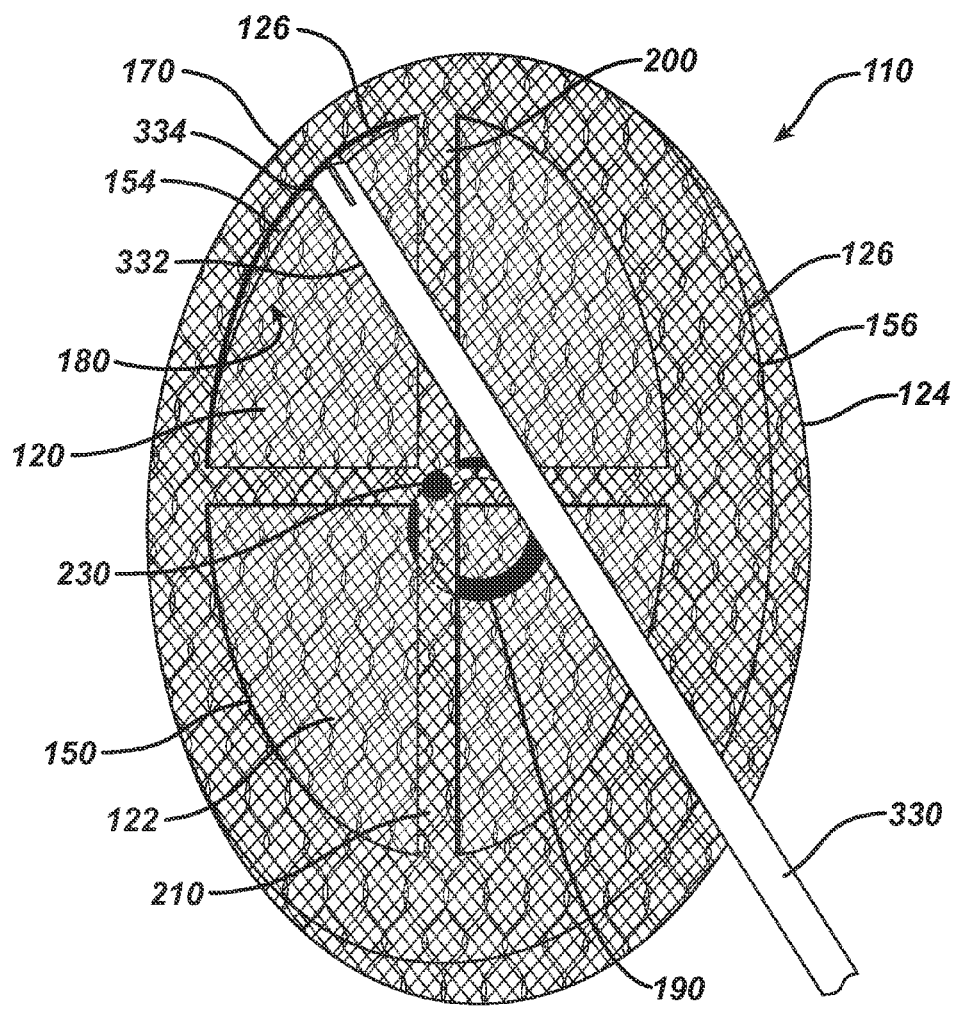
FIG. 8 illustrates the implant of FIG. 6, wherein the distal end of a surgical tacking instrument has been moved into position to affix the top skirt to an interior surface of a body wall; the top position indicating feature is offset indicating that an adjacent section of the skirt has rolled over, and a diametrically opposed section of the base member has rolled up.
Figure 9:
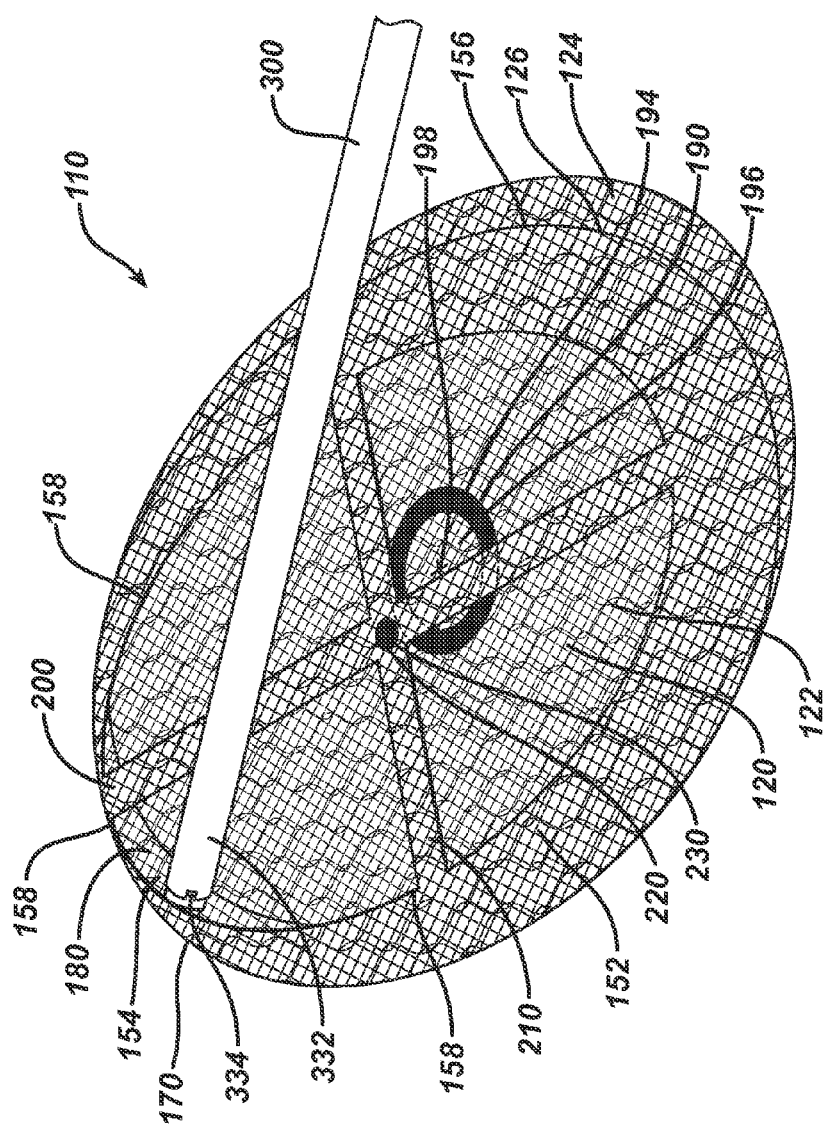
FIG. 9 is a perspective view of the implant and tacking instrument distal end of FIG. 8.
Figure 10:
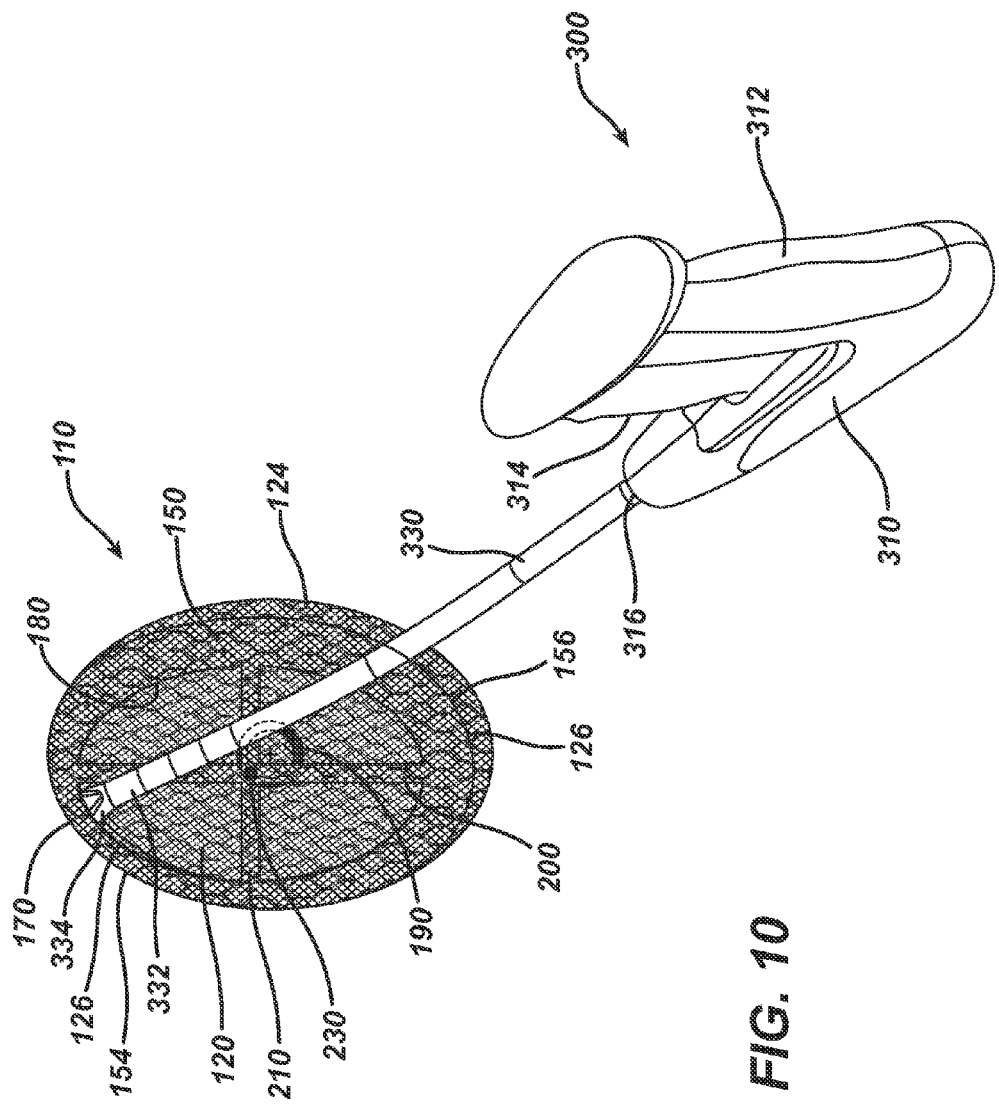
FIG. 10 is a perspective view of the implant of FIG. 8 illustrating the entire surgical tacking instrument; the top position indicating feature offset is visible to the surgeon indicating a partial rollover of the top skirt.

When the implant 110 is in the rest or neutral position as seen in FIG. 6, the second indicating feature 230 is seen by the surgeon to be substantially aligned with the center of the first indicating feature. As seen in FIG. 7, the second indicating feature 230 has moved out of alignment with the center of the first indicating feature 190, and is aligned with the periphery of the first indicating feature. A section 170 of the skirt member 150 is seen to have displace or rolled over the outer periphery 126 of base member 120 creating a condition referred to as a "rollover"; similarly a section of the bottom side 124 has seen to have rolled up over outer periphery 126. Referring to FIGS. 8, 9 and 10, the distal end 332 and tip 334 of a surgical tacking instrument 300 have been placed adjacent to the exterior periphery 158 of skirt member 150 and pocket 180. In FIGS. 8, 9 and 10, the surgeon has inserted distal end 332 and tip 334 of the surgical instrument 300 into the pocket 180 to secure the implant 100 to tissue, but has inadvertently moved section 170 beyond periphery 126 creating a rollover adjacent to the tip 334 and a second "roll up" on the opposite side. A rollover condition will be apparent to the surgeon when the center of the second indicating feature 230 is at least partially out of alignment with the center of the first indicating feature 190. This visual input will allow the surgeon to correct the position of the distal end 332 and distal tip 334 so that the rollover section 170 is remediated. Conversely, if the second indicating feature 230 is substantially in alignment with the first indicating feature 230 when the surgeon locates the distal tip 334 next to periphery 158 of skirt member 150, then this will indicate proper placement of fixating tacks about the outer periphery 158 of skirt member 50 without a rollover. If desired, in another embodiment a second indicating feature without connecting members may be utilized and positioned on the skirt member such that the relative positions of the first and second indicating features are apparent and any movement of the second indicating feature with respect to or relative to the first indicating feature indicates a rollover of at least a section of the skirt member.

Additional embodiments of the implant 110 (not shown) may eliminate the connecting members 200 and 210 while retaining the second indicating feature 230, and locate the second indicating feature 230, for example, on one or more locations on skirt member 150 such that movement of the one or more indicating features 230 with respect to the first indicating feature 190 indicates a rollover condition of one or more sections of skirt member 150.

The following examples are illustrative of the principles and practice of the present invention, although not limited thereto.

EXAMPLE 1

A patient with a ventral or incisional hernia is prepared for an open hernia repair procedure in the following manner.

The skin area surrounding the hernia is scrubbed with a conventional antimicrobial solution such as betadine. The patient is administered conventional general anesthesia in a conventional manner by induction and inhalation. The surgeon then initiates the surgical procedure by making an incision in the skin and subcutaneous tissue overlying the hernia. In the case of planned intra-peritoneal mesh placement, the hernia sac is opened. The edges of the healthy fascia around the defect are examined and any attachments of the viscera to the abdominal wall are divided to create a free space for fixation of the mesh.

At this point in the procedure, the surgeon then prepares a tissue repair hernia patch 10 of the present invention having a base member, a skirt and a position indicating feature for insertion through the abdominal wall defect and into the abdominal cavity such that the top side of the skirt is adjacent to the peritoneum surrounding the defect, and the bottom side of the mesh device is facing down toward the patient's viscera. Stay sutures may be placed through the mesh into the abdominal tissue as desired, i.e., at the four compass points of the mesh (North, South, East, West). The repair device is fixated with a conventional surgical tacking instrument or other means of fixation. The tacking instrument is inserted through the opening of the skirt into the pocket such that the distal end of the tacking instrument is positioned adjacent to the peripheries of the base member and the skirt member. The periphery of the skirt member is then fixated to the parietal wall using a plurality of tacks in a crown configuration. During the fixation process with the tacks, the surgeon observes the positioning indicator feature prior to firing off a tack. If the position indicator shows that the section of mesh being secured is displaced indicating a rollover, the surgeon repositions the tip of the tacking instrument to correct the displacement, and then secures that section of the skirt member by firing a tack. The tacking instrument is removed from the implant when the mesh member has been effectively and securely attached by the tacks to the parietal wall. The hernia defect may be primarily closed if desired. The skin incision is closed using appropriate suturing or closure techniques, and the incision is appropriately bandaged and the patient is moved to a recovery room.

The novel skirted tissue repair devices of the present invention have numerous advantages. The advantages include providing positioning features which alert the surgeon to a roll over condition, assisting the surgeon in providing an optimal surgical repair, and producing a superior patient outcome.

Although this invention has been shown and described with respect to detailed embodiments thereof, it will be understood by those skilled in the art that various changes in form and detail thereof may be made without departing from the spirit and scope of the claimed invention.

I claim:

1. A tissue repair implant, the implant comprising:
   a bottom planar base member having a top surface, a bottom surface and an outer periphery;
   a top planar skirt member having a bottom surface, and a top surface, an inner periphery and an outer periphery, wherein the skirt member extends inwardly about the outer periphery of the planar base member such that a surgical instrument can be inserted between the top surface of the planar base member and the bottom surface of the skirt member;
   an access opening associated with the skirt member; and,
   an indicating feature associated with the bottom base member and aligned with the inner periphery of the skirt member wherein the indicating marker is not visible when the skirt member is in a first neutral position such that no part of the skirt member extends beyond the outer periphery of the base member, and wherein at least a section of the indicating marker is exposed and visible when a section of the skirt member is displaced radially outward beyond the outer peripheries of the skirt member and bottom base member.

2. The tissue repair implant of claim 1, additionally comprising a polymeric layer on at least one side of the base member.

3. The tissue repair implant of claim 1, additionally comprising an adhesion barrier on at least one side of the base member.

4. The implant of claim 1, wherein the base member comprises a mesh.

5. The implant of claim 1, wherein the base member comprises a fabric.

6. The implant of claim 5 wherein the fabric is woven.

7. The implant of claim 5 wherein the fabric is nonwoven.

8. The implant of claim 7 wherein the nondegradable polymer is selected from the group consisting of polypropylene, polyester, nylon, and ultra-high molecular weight polyethylene.

9. The implant of claim 1, wherein the base member comprises an expanded polymeric film.

10. The implant of claim 1, wherein the base member comprises a biocompatible, nondegradable polymer.

11. The implant of claim 1, wherein the base member comprises a bioabsorbable polymer.

12. The implant of claim 11, wherein the bioabsorbable polymer is selected from the group consisting of polylactides, polyglycolides, polydioxanones, polycaprolactones, copolymers of glycolides and trimethylene carbonate, and copolymers of lactides and trimethylene carbonate, and copolymers and blends thereof.

13. The patch of claim 1, wherein the base member comprises a biocompatible nondegradable polymer and a bioabsorbable polymer.

14. A method of repairing a body wall defect using the tissue repair implant of claim 1, comprising the steps of:
    securing the skirt member of the implant to tissue proximate to the defect with surgical fasteners; and,
    viewing the position of the indicating feature to detect a rollover of the skirt member.

15. A tissue repair implant, the implant comprising:
    a bottom planar base member having a top surface, a bottom surface and an outer periphery, the base member having a first longitudinal axis and a first latitudinal axis and a first intersection point at the intersection of the first longitudinal axis and the first latitudinal axis;
    a first position indicator associated with the bottom base member and centered on the first intersection point;
    a top planar skirt member having a bottom surface, and a top surface, an inner periphery and an outer periphery, wherein the skirt member extends inwardly about the outer periphery of the planar base member such that a surgical instrument can be inserted between the top surface of the planar base member and the bottom surface of the skirt member, the skirt member having a second longitudinal axis and a second latitudinal axis and a second intersection point at the intersection of the second longitudinal axis and second latitudinal axis;
    an access opening associated with the skirt member;
    a first connecting member connecting the inner periphery of the skirt member in alignment with the first longitudinal axis and the second longitudinal axis;

a second connecting member connecting the inner periphery of the skirt member in alignment with the first latitudinal axis and the second latitudinal axis and intersecting the first connecting member at a second intersection point; and, a second position indicator associated with the second intersection point for determining the position of the second intersection point with respect to the first intersection point, wherein a misalignment of the first and second position indicators is associated with a rollover of a section of the skirt member.

16. The tissue repair implant of claim 15, additionally comprising a polymeric layer on at least one side of the base member.

17. The tissue repair implant of claim 15, additionally comprising an adhesion barrier on at least one side of the base member.

18. The implant of claim 15, wherein the base member comprises a mesh.

19. The implant of claim 15, wherein the base member comprises a fabric.

20. The implant of claim 19 wherein the fabric is woven.

21. The implant of claim 19 wherein the fabric is non-woven.

22. The implant of claim 15, wherein the base member comprises a biocompatible, nondegradable polymer.

23. The implant of claim 22 wherein the nondegradable polymer is selected from the group consisting of polypropylene, polyester, nylon, and ultra-high molecular weight polyethylene.

24. The implant of claim 15, wherein the base member comprises a bioabsorbable polymer.

25. The implant of claim 24, wherein the bioabsorbable polymer is selected from the group consisting of polylactides, polyglycolides, polydioxanones, polycaprolactones, copolymers of glycolides and trimethylene carbonate, and copolymers of lactides and trimethylene carbonate, and copolymers and blends thereof.

26. The implant of claim 15, wherein the base member comprises a biocompatible nondegradable polymer and a bioabsorbable polymer.

27. A method of repairing a body wall defect using the tissue repair implant of claim 15, comprising the steps of:
    securing the skirt member of the implant to tissue proximate to the defect with surgical fasteners; and,
    viewing the position of the second indicating feature with respect to the first indicating feature to detect a rollover of the skirt member.

28. A tissue repair implant, the implant comprising:
    a bottom planar base member having a top surface, a bottom surface and an outer periphery;
    a first position indicator associated with the bottom base member
    a top planar skirt member having a bottom surface, and a top surface, an inner periphery and an outer periphery, wherein the skirt member extends inwardly about the outer periphery of the planar base member such that a surgical instrument can be inserted between the top surface of the planar base member and the bottom surface of the skirt member;
    an access opening associated with the skirt member; and,
    a second position indicator associated with the skirt member for determining the position of the second position indicator with respect to the first position indicator, wherein a movement of the second position indicator with respect to the first position indicator is an indication of a rollover of a section of the skirt member.

* * * * *